United States Patent
Katoh et al.

(10) Patent No.: US 7,798,983 B2
(45) Date of Patent: Sep. 21, 2010

(54) WALKING ASSISTANCE DEVICE

(75) Inventors: Hisashi Katoh, Wako (JP); Takashi Hirata, Wako (JP); Taiji Koyama, Wako (JP); Takako Fujii, Kyoto (JP); Yoshirou Koyama, Kyoto (JP)

(73) Assignee: Honda Motor Co., Ltd., Minato-Ku, Tokyo (JP)

( * ) Notice: Subject to any disclaimer, the term of this patent is extended or adjusted under 35 U.S.C. 154(b) by 139 days.

(21) Appl. No.: 10/557,733

(22) PCT Filed: Mar. 15, 2004

(86) PCT No.: PCT/JP2004/003402

§ 371 (c)(1), (2), (4) Date: Jun. 23, 2006

(87) PCT Pub. No.: WO2004/103246

PCT Pub. Date: Dec. 2, 2004

(65) Prior Publication Data

US 2007/0055189 A1 Mar. 8, 2007

(30) Foreign Application Priority Data

May 21, 2003 (JP) .............................. 2003-143494

(51) Int. Cl.
*A61F 5/00* (2006.01)
*A61H 1/00* (2006.01)

(52) U.S. Cl. .............................. 602/16; 602/19; 602/23; 601/5

(58) Field of Classification Search .................. 602/19, 602/16, 23, 26, 27; 607/49, 48; 601/5, 33, 601/34, 35; 623/27; 482/66, 124
See application file for complete search history.

(56) References Cited

U.S. PATENT DOCUMENTS 5,020,790 A * 6/1991 Beard et al. .................... 482/4
5,476,441 A * 12/1995 Durfee et al. ................. 602/23

FOREIGN PATENT DOCUMENTS

| JP | 58-41556 | 3/1983 |
|---|---|---|
| JP | 58-163364 | 9/1983 |
| JP | 61-228854 | 10/1986 |
| JP | 7-163607 | 6/1995 |
| JP | 9-103443 | 4/1997 |
| JP | 11-290360 | 10/1999 |
| JP | 2001-214303 | 8/2001 |

* cited by examiner

*Primary Examiner*—Patricia M Bianco
*Assistant Examiner*—Ophelia Hawthorne
(74) *Attorney, Agent, or Firm*—Squire, Sanders & Dempsey, LLP

(57) ABSTRACT

In order to provide a walking assistance device that can avoid hampering the motion of the muscles of the user and will not move out of place inadvertently when worn by the user, principal engagement points of a support member for securely mounting an assisting force generator, which is disposed on a side of at least one joint of a lower limb to provide an assisting force to a movement of the lower limb, are provided at portions where a relatively small amount of movement of skin occurs when a trunk or joint is moved. In this way, the support member can be fastened firmly to the portions where an amount of movement of the skin is small and therefore it is possible to reduce the uncomfortable pressure caused during motion while preventing the support member from inadvertently moving out of place.

4 Claims, 6 Drawing Sheets

WALKING ASSISTANCE DEVICE

REFERENCE TO PRIOR RELATED PATENT APPLICATION

This application claims the benefit of priority from the national stage entry of PCT/JP04/03402, International Filing Date: Mar. 15, 2004 claims foreign priority to 2003-143494, filed May 21, 2003.

TECHNICAL FIELD

The present invention relates to a walking assistance device for providing an assisting force to the movement of the lower limb, i.e., mainly of the hip joint or knee joint.

BACKGROUND ART

Various proposals have been made for a walking assistance device that is adapted to mount an actuator to the hip joint or knee joint of a person having a walking impediment due to injury, disease or weakened muscle resulting from aging, so that the power from the actuator can be used to assist the movement of the lower limb.

Conventionally, it was common in such a walking assistance device to fixedly mount the actuator to the lower limb via a support member fastened on the hip, thigh or lower leg portion by tightening a belt or the like.

DISCLOSURE OF THE INVENTION

However, in the prior art devices as disclosed in Japanese Patent Application Laid-Open Publication No. 58-163364 (FIGS. 1-4) or Japanese Patent Application Laid-Open Publication No. 7-163607 (FIG. 1), when a person uses the assistance device for the purpose of assisting the weakened muscle, the fastening of the support member around the thigh, where the cross section (or circumferential length) of the muscle changes significantly with the expansion/contraction of the muscle, can undesirably hamper the movement of the muscle. For example, if the support member is adjusted so as to snugly fit around the thigh when a person is standing and the muscle is expanded straight, the support member will impose a strong pressure onto the thigh when the person crouches down and the muscle contracts. On the other hand, if the support member is adjusted so as to snugly fit around the thigh when the person is in a crouching state, the support member will become loose when the person stands up.

It may be conceived to form the support member from a flexible material such as a rubber material. However, in order to prevent the support member from becoming loose, a fastening force larger than a certain level is nonetheless required, and it was quite difficult to achieve a support member that will not cause any pain or discomfort to the user.

The present invention is made to solve the above problems in the prior art, and a primary object of the present invention is to provide a walking assistance device that can avoid hampering the motion of the muscles of the user and will not move out of place inadvertently when worn by the user.

According to the present invention, such an object can be accomplished by providing a walking assistance device in which principal engagement points of a support member (hip support member 1 and/or lower leg support member 2) for securely mounting an assisting force generator (hip joint actuator 10 and/or knee joint actuator 26), which is disposed on a side of at least one joint of a lower limb to provide an assisting force to a movement of the lower limb, are provided at portions where a relatively small amount of movement of skin occurs when a trunk or joint is moved.

Thus, by firmly fastening the support member to the portions where an amount of movement of the skin is small, it is possible to reduce the uncomfortable pressure caused upon the wearer during motion while preventing the support member from moving out of place inadvertently because the circumferential length change due to expansion/contraction of the muscles is small at such portions.

Preferably, a hip joint actuator (10) is secured on a side of a hip joint via a hip support member (1) adapted to engage a lower abdominal portion around a lower part of an abdominal muscle as well as a region extending from right and left iliac crests to a backside of a sacroiliac joint, or a knee joint actuator (26) is secured on a side of a knee joint via a lower leg support member (2) adapted to fit on a region extending from lateral sides of an upper part of a shank to an upper part of an Achilles tendon while avoiding a calf muscle. The hip support member presses the so-called "tanden" whereby the pressure reflex of the pelvis causes the pressure to be applied to the whole abdominal cavity, stabilizing the upright posture. Also, the load associated with the constraining pressure of the belt (15) applied to the lower abdominal portion can be reduced. Further, the lower leg support member allows the actuator, such as an electric motor, for assisting extension/flexion of the knee joint to be disposed in place so as not to hamper the muscle motion of the user as well as not to undesirably move out of place.

Particularly, it is preferable that the engagement points of the lower leg support member include a foot portion (31). This allows the weight of the whole device to be supported by the ground and thus can reduce the load on the body.

Further, the device may preferably comprise: a drive unit (3) formed by joining a hip joint actuator (10) for providing an assisting force to a movement of a hip joint and a knee joint actuator (26) for providing an assisting force to a movement of a knee joint; a hip support member (1) for securing the hip joint actuator on a side of the hip joint; and a lower leg support member (2) for securing the knee joint actuator on a side of the knee joint. Thus, the whole device including the assisting force generators can be constituted by three separate members, and this can improve the wearability of the device.

Further preferably, an upper end of the drive unit may be attached to the hip support member and a lower end of the drive unit may be attached to the lower leg support member. This allows the drive reaction force of the actuators mounted at either end of the drive unit to be properly supported by the associated support members.

BEST MODE FOR CARRYING OUT THE INVENTION

Figure 1:
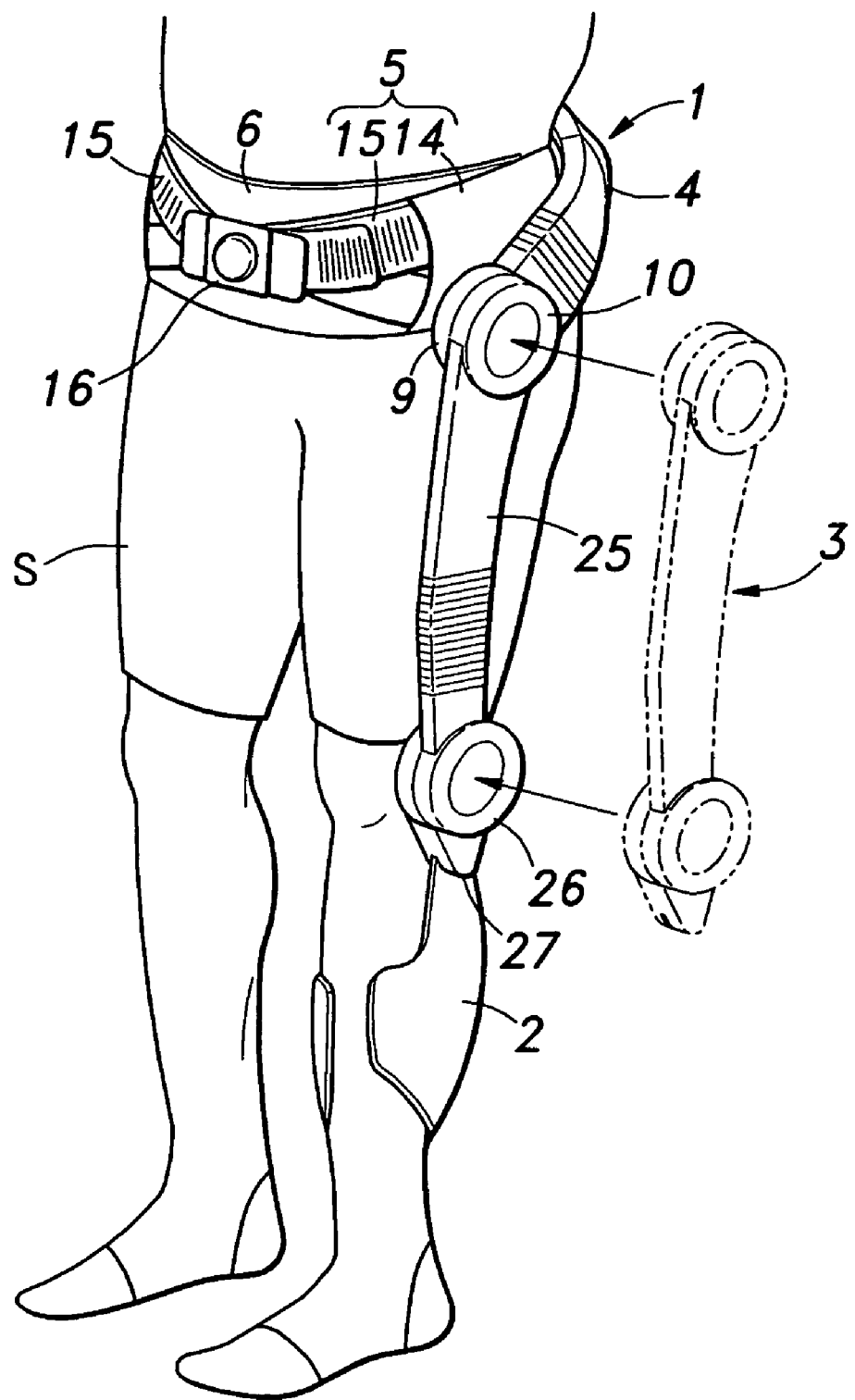
FIG. 1 is a perspective view showing a lower body on which a walking assistance device of the present invention is fitted.

FIG. 1 shows a walking assistance device of the present invention as worn on a user's body. The walking assistance device consists of a hip support member 1, lower leg support member 2 and a drive unit 3 for generating an assisting force, where the hip support member 1 and the lower leg support member 2 are secured on a lower limb and a rotational torque generated by the drive unit 3 is transmitted to the lower limb via the hip and lower leg support members, to whereby provide a force for supplementing a reduced muscle power.

Figure 2:
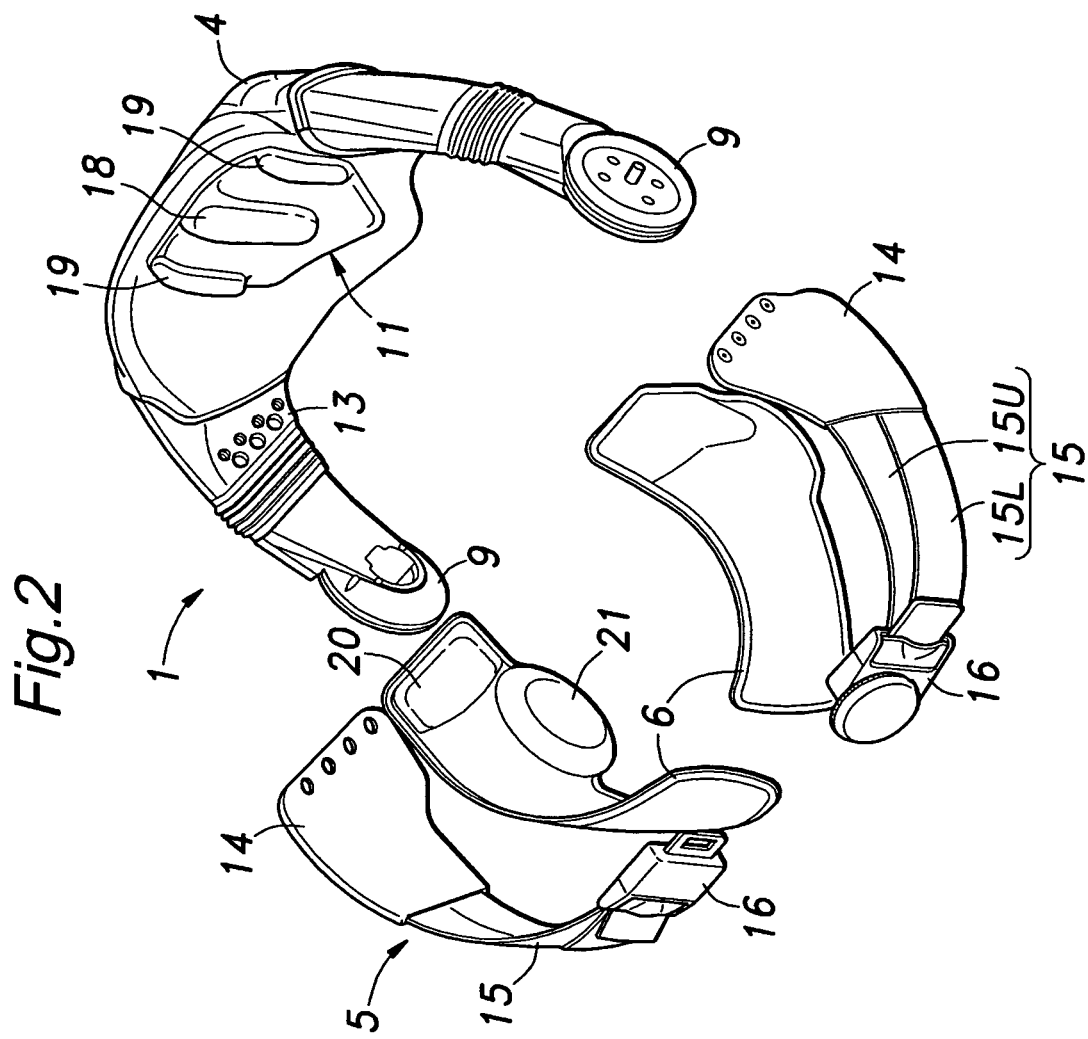
FIG. 2 is an exploded perspective view showing the structure of a hip support member of the walking assistance device according to the present invention.

The hip support member 1 comprises a back support 4, belt portion 5 and lining portion 6, as shown in FIG. 2.

Figure 3:
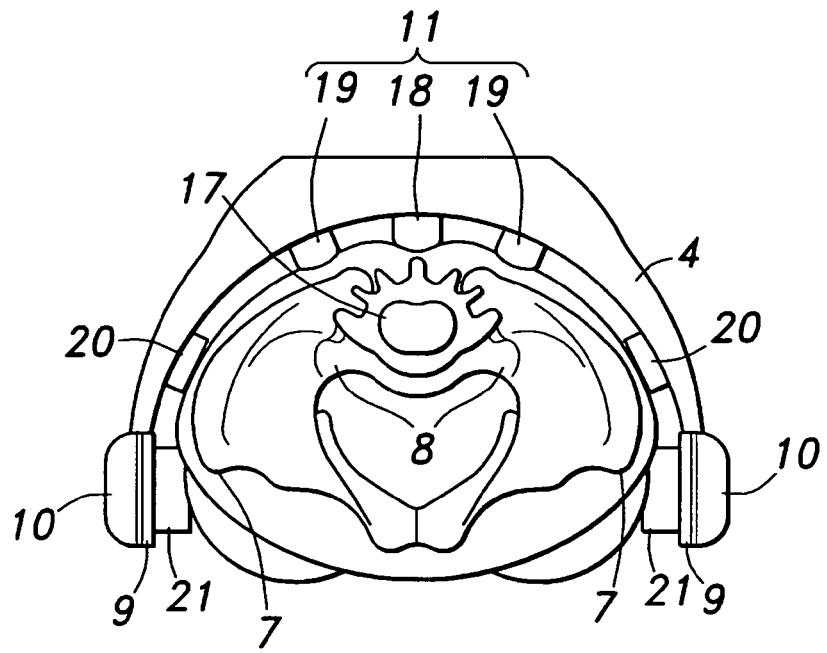
FIG. 3 is an explanatory drawing showing the relationship between a back support and the user's body.

Additionally referring to FIG. 3, the back support 4 is substantially of the shape of letter-U as seen in plan view so that it abuts a region of the body extending from right and left iliac crests (front ends of the pelvic bone) 7 to the backside of the sacroiliac joint (joint between the vertebrae and pelvic bone) 8, and consists of a substantially rigid body so as to withstand the drive force generated by a hip joint actuator 10, which consists of an electric motor equipped with a reduction gear or the like and is mounted on a hip drive source mount 9 provided at each of the right and left ends of the back support 4. A rear portion of the back support 4 has a hollow space so that a control circuit and a battery for supplying electric power to the control circuit as well as to the electric motor are accommodated therein, though not explicitly shown in the drawings. Further, at a portion of the back support 4 that directly abuts the user's body is provided a cushioning pad 11.

The belt portion 5 is made of a relatively rigid material and comprises: a pair of right and left bases 14 attached by means of bolts to inner sides of belt joints 13 provided at right and left side portions of the back support 4; a pair of right and left web parts 15 fixed to front ends of the bases 14; and a pair of right and left buckles 16 attached to front ends of the web parts 15. The inner surface of the belt portion 5, i.e., the surface facing the hip portion of the user's body, is adapted to be attached with the lining portion 6 for protection by means of loop and hook fastener or the like.

The cushioning pad 11 provided to the back support 4 comprises a center pad 18 abutting a depression extending along a lumbar vertebra 17 and a pair of side pads 19 abutting laterally outer regions of erector spine muscles slightly jutting out backward at right and left of the lumbar vertebra 17. Further, the lining portion 6 comprises iliac pads 20 abutting the iliac crests 7. Thus, a total of five pads abut principal portions of the hip to keep the back support 4 from moving out of place. Further, because direct contact of the hip power transmitter 9 with the user's body would cause pain to the user and could impart a large impact on the body if the user happens to fall, hip joint pads 21 are provided to the lining portion 6 so as to be interposed between the user's body and the hip power transmitter 9 and reduce the impact and pain.

Each of the web parts 15 comprises a pair of upper and lower plain weave belts secured to the associated base 14, and the front ends of the belts are joined together and attached to the corresponding buckle 16 so that they form a shape of letter-V that converges in the front direction. The upper belt 15U of each web part 15 extends from the joint with the base 14 disposed at a position corresponding to the iliac crest 7 toward the buckle 16 disposed at an intermediate portion ("tanden") between the navel and pubic bone along a direction of the extension of muscle fibers of the abdominal external oblique muscle. The lower belt 15L of the web part 15 extends from the joint with the base 14 disposed on a side of the hip joint toward the buckle 16 along a direction of fibers of the abdominal internal oblique muscle.

The upright posture of the spine is maintained by the balance of back muscle, pectoral muscle and abdominal muscle. The weakening of muscles of a person having walking impediment applies not only to the muscles of lower limb but also to the back, pectoral or abdominal muscles. Particularly, the weakening of the abdominal muscle can lower the abdominal cavity and cause the spine to bend in the shape of letter-S as seen in side view, thus making it difficult to maintain the upright posture during walking. According to the present invention, the buckle 16 is positioned at a center of lower abdomen called "tanden" where the rectus abdominal muscle, abdominal external oblique muscle, abdominal internal oblique muscle, transverses abdominal muscle, etc. which play an important role in keeping the upright posture, overlap each other, and a tightening force is applied to the web parts 15 so that the back support 4 fitted on a region extending from the right and left iliac crests 7 to the backside of the sacroiliac joint functions to correct the curve of the spine and stabilize the pelvis to achieve a proper posture and at the same time increase the abdominal cavity pressure to lift up the viscera to proper positions. Further, because the web parts 15 abut the lower abdominal portion with a relatively large contact area, the pressure applied to the abdominal cavity can be distributed evenly over the whole lower abdominal portion, thus reducing the uncomfortable pressure felt by the user.

Figure 4:
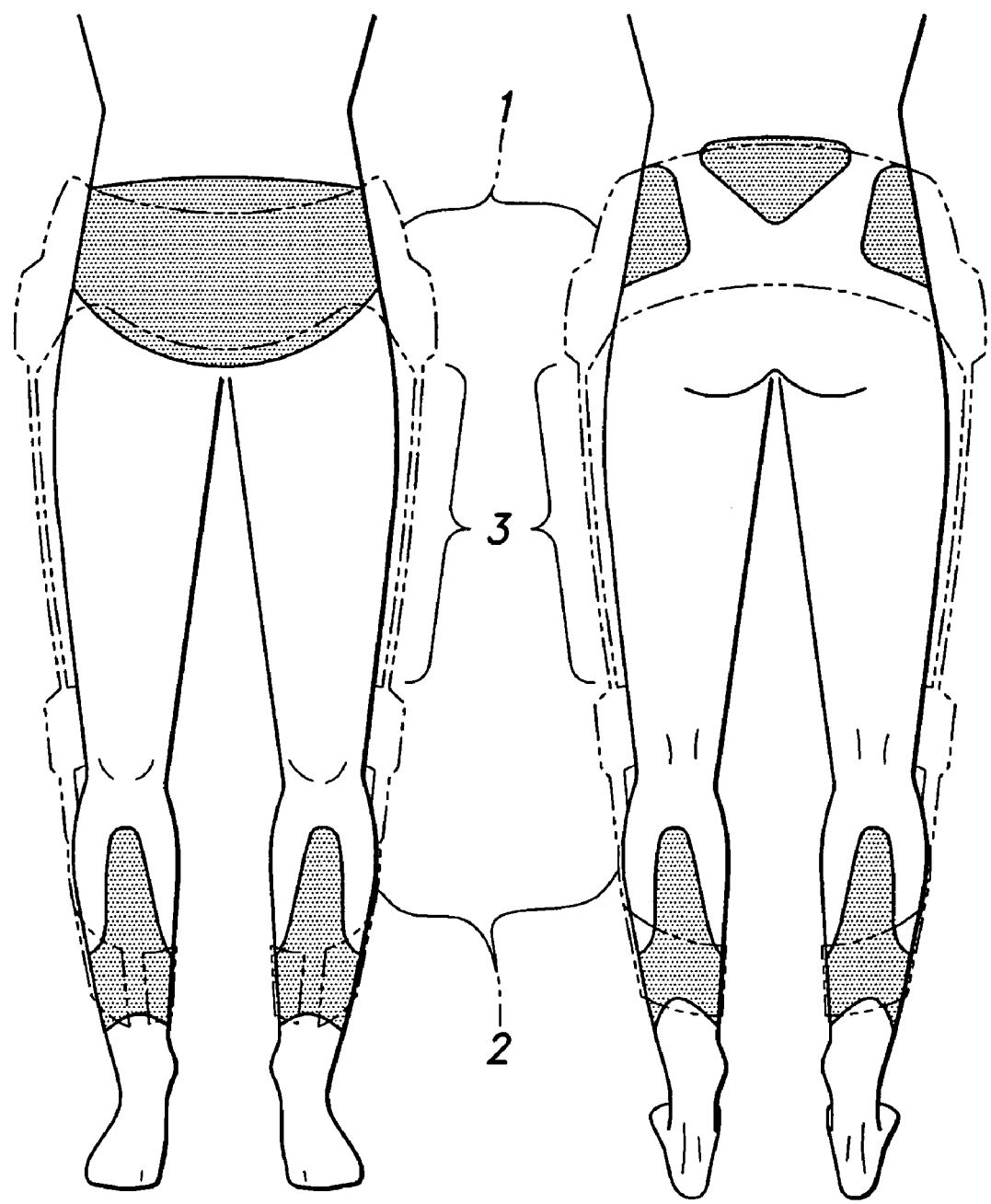
FIG. 4 is an explanatory drawing showing the relationship between the device of the present invention and the user's body.

As shown in FIG. 4, the back support 4 and belt portion 5 are adapted to engage the body portions (hatched regions of the hip in the drawing) where a relatively small amount of movement of skin occurs as the trunk or lower limb joint is moved. Owing to this feature, the motion of the hip joint relating to the lifting up and down of the thigh as well as the forward bending of the trunk will not be hampered, and the device will not be affected by the change in the circumferential length of the thigh due to expansion/contraction of the femoral muscles.

According to the above structure, the principal engagement points (five pads 18, 19, 20) of the back support 4 are provided on the backside, which has a relatively small difference in shape from person to person, and therefore, it is only necessary to change the belt portion 5 to cope with wearers of different builds and the back support 4 can be used in common, which contributes to a lower manufacturing cost of the hip support member 1.

Figure 5:
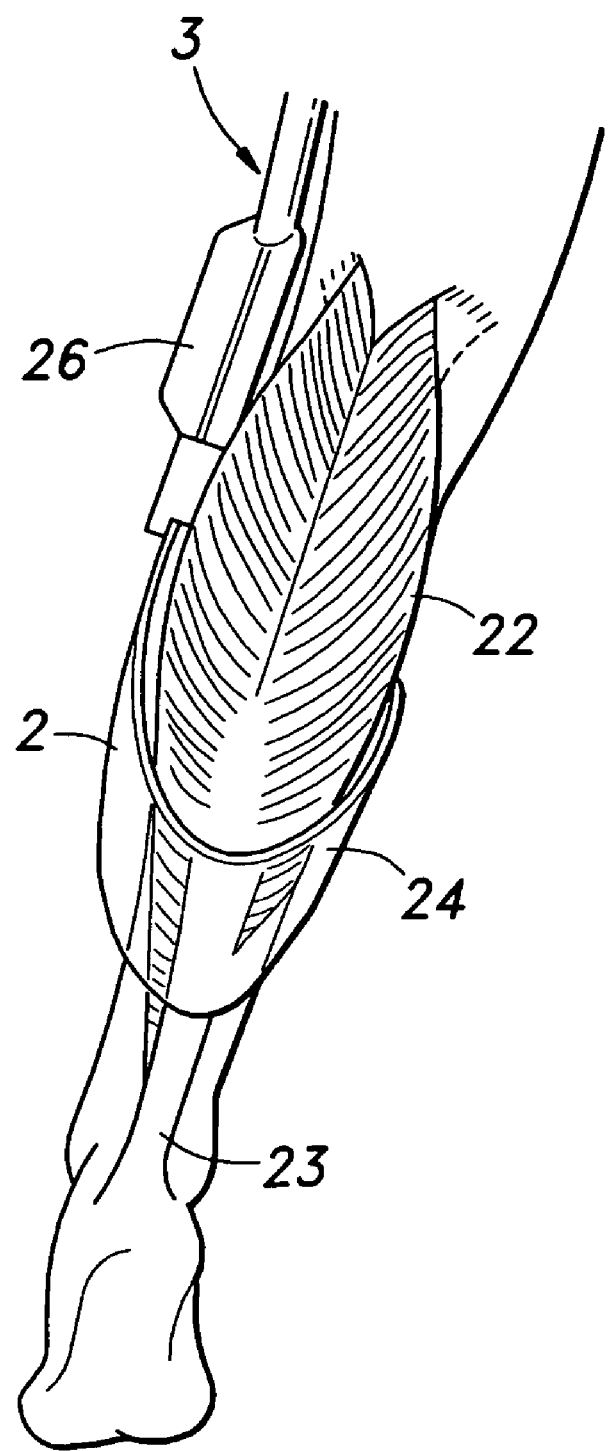
FIG. 5 is an explanatory drawing showing a lower leg support member fitted on a lower leg portion.

On the other hand, as also shown in FIG. 5, the lower leg support member 2 comprises a band-like member 24 wound around the lower leg portion so as to cover the region where the skin movement is relatively small (hatched regions of the lower leg in FIG. 4), i.e., region extending from lateral sides of an upper part of the anterior tibia muscle to the portion between a lower part of the calf muscle 22 and an upper part of the Achilles tendon 23. According to such a structure, it can be avoided to place the principal engagement points of the lower leg support member 2 on the calf, of which circumferential length can vary with the extension/flexion of the knee, or on the Achilles tendon where the skin moves with the motion of the ankle, and therefore it is possible to securely fasten the lower leg support member 2 on the lower leg with an abundant tightening force.

Figure 6:
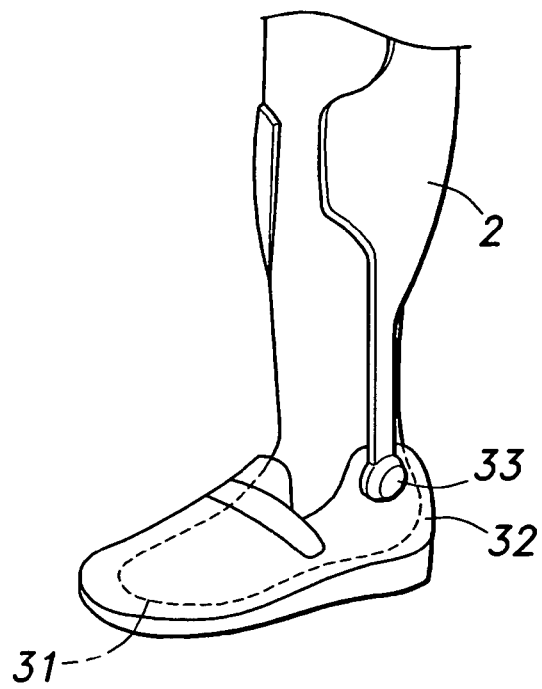
FIG. 6 is a perspective view of a principal part of another embodiment of the lower leg support member.

As shown in FIG. 6, the lower end of the lower leg support member 2 may be connected to a portion of a shoe 32 fitted on a foot 31 that corresponds to an ankle. In this way, the whole weight of the device can be supported by the ground and this can reduce the load imposed upon the wearer's body. It should be noted that if the joint 33 between the lower leg support member 2 and the shoe 32 is rotatable so as not to hamper the movement of the ankle during walking, significant discomfort to the user can be avoided because the shoe itself is made so as to be capable of coping with the movement of the toes.

Figure 7:
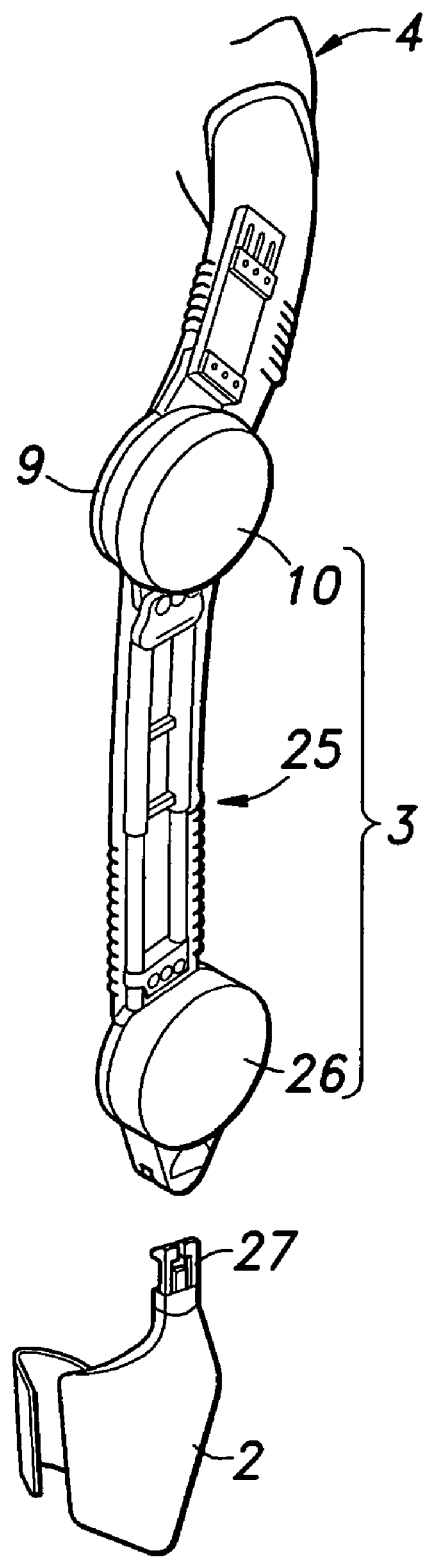
FIG. 7 is a perspective view of a drive unit.

Additionally referring to FIG. 7, the drive unit 3 comprises a hip joint actuator 10 and a knee joint actuator 26, each consisting of an electric motor equipped with a reduction gear or the like, where the actuators are attached to either end of a link bar 25 which is expandable and contractable in a telescopic fashion. The drive unit 3 is adapted so as to be detachable from the hip drive source mount 9 provided to the back support 4 at a position corresponding to a side of the hip joint as well as from a knee drive source mount 27 provided to the lower leg support member 2 at a position corresponding to a side of the knee joint. Because the hip support member 1, lower leg support member 2 and drive unit 3 are provided as separate members from one another, the user will not be required to take unnatural posture and can put on/off the device easily without help of other person.

If the device of the present invention is worn over a spat S for exercise that is adapted to provide a specific muscle(s) with a tightening force that is equivalent to that produced by taping (see Japanese Patent Application Laid-Open No. 2001-214303), the device can function even more effectively to improve the motion ability of the user in cooperation with the muscle support effect resulting from the tightening force produced by the fibers forming the spat S. Also, if the drive torque is effected in reverse, the device of the present invention can apply a load torque upon the joint, and therefore the device can be used not only as a motion assisting device but also as a load generator for medical treatment, rehabilitation or training for muscle development.

INDUSTRIAL APPLICABILITY

As described above, according to the present invention, the following advantages can be obtained:
1. Because the walking assistance device for providing an assisting force to the movement of the hip joint or knee joint of the lower limb is fitted on portions of the body that are hard to be affected by expansion/contraction of the muscles that occurs with motion, the device will not be affected by a change in the circumferential length of the muscle due to the expansion/contraction and therefore the uncomfortable pressure caused during motion can be reduced. Further, because the device is fitted on the portion where only a small amount of movement of skin occurs during motion, the device can be kept from inadvertently moving out of place.
2. Because the hip support member is adapted to engage a lower abdominal portion as well as a region extending from the right and left iliac crests to the backside of the sacroiliac joint, it is possible to press the so-called "tanden" whereby the pressure reflex of the pelvis causes the pressure to be applied to the whole abdominal cavity, and this makes it easier for the user to keep a proper posture steadily and reduces the load associated with the constraining pressure of the belt applied to the lower abdominal portion. Further, because the lower leg support member is adapted to fit on a region extending from the lateral sides of an upper part of the shank to an upper part of the Achilles tendon while avoiding the calf muscle, the actuator for assisting extension/flexion of the knee joint can be disposed in place so as not to hamper the muscle motion of the user as well as not to undesirably move out of place.
3. Owing to the structure that the engagement points of the lower leg support member include a foot portion, the weight of the whole device can be supported by the ground and this can reduce the load on the body.
4. Because the whole device including the assisting force generators is constituted by three separate members consisting of: the drive unit formed by joining the hip joint actuator and the knee joint actuator; the hip support member; and the lower leg support member, the wearability of the device can be improved.
5. Because the upper end of the drive unit is attached to the hip support member while the lower end of the drive unit is attached to the lower leg support member, the drive reaction force of the actuators mounted at either end of the drive unit can be properly supported.

The invention claimed is:
1. A walking assistance device, comprising: an assisting force generator disposed on a side of at least one joint of a lower limb to provide an assisting force which reduces the amount of muscle power used when generating a movement of the lower limb, the assisting force being a rotational torque generated by a drive unit of the assisting force generator; and at least one of a hip support member for securely mounting the assisting force generator on the side of a hip joint and a lower leg support member for securely mounting the assisting force generator on the side of a knee joint, wherein principal engagement points of the hip support member for securely mounting the assisting force generator on the side of the hip joint and those of the lower leg support member for securely mounting the assisting force generator on the side of the knee joint are provided at portions where a relatively small amount of movement of skin occurs when a trunk or joint is moved and that are hard to be affected by expansion/contraction of muscles and the lower leg support member is adapted to fit on a region extending from lateral sides of an upper part of a shank to a portion between a lower part of a calf muscle and an upper part of an Achilles tendon while avoiding the calf muscle and the Achilles tendon to secure the assisting force generator on the side of the knee joint wherein the engagement points of the lower leg support member include a foot portion.

2. The walking assistance device according to claim 1, comprising:
a drive unit formed by joining a hip joint actuator for providing an assisting force to a movement of a hip joint and a knee joint actuator for providing an assisting force to a movement of a knee joint;
a hip support member for securing the hip joint actuator on a side of the hip joint; and
a lower leg support member for securing the knee joint actuator on a side of the knee joint.

3. The walking assistance device according to claim 2, wherein an upper end of the drive unit is attached to the hip support member, and a lower end of the drive unit is attached to the lower leg support member.

4. The walking assistance device according to claim 1, wherein the hip support member is adapted to engage a lower abdominal portion around a lower part of an abdominal muscle as well as a region extending from right and left iliac crests to a backside of a sacroiliac joint to secure the assisting force generator on the side of the hip joint.

* * * * *